(12) United States Patent
Lu et al.

(10) Patent No.: US 11,883,517 B2
(45) Date of Patent: Jan. 30, 2024

(54) EXTERNAL DERMAL COMPOSITION AND METHOD FOR BEAUTIFYING SKIN

(71) Applicant: National Tsing Hua University, Hsinchu (TW)

(72) Inventors: Tsai-Te Lu, Hsinchu (TW); Chieh-Cheng Huang, Hsinchu (TW); Han Chiu, Hsinchu (TW); Wei-Ping Wang, Hsinchu (TW); Ruei-Ting Wang, Hsinchu (TW); Yi-Cian Lai, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 48 days.

(21) Appl. No.: 17/571,838

(22) Filed: Jan. 10, 2022

(65) Prior Publication Data

US 2023/0089444 A1 Mar. 23, 2023

(30) Foreign Application Priority Data

Sep. 12, 2021 (TW) .................................. 110133933

(51) Int. Cl.
| | |
|---|---|
| *A61P 17/02* | (2006.01) |
| *A61K 8/58* | (2006.01) |
| *A61K 8/19* | (2006.01) |
| *A61K 31/295* | (2006.01) |
| *A61K 33/26* | (2006.01) |
| *A61Q 19/08* | (2006.01) |
| *A61Q 9/02* | (2006.01) |

(52) U.S. Cl.
CPC ................ *A61K 8/58* (2013.01); *A61Q 19/08* (2013.01)

(58) Field of Classification Search
CPC . A61K 8/58; A61K 8/19; A61K 8/585; A61K 31/295; A61K 33/26; A61Q 19/08; A61Q 19/02; A61P 17/02
See application file for complete search history.

(56) References Cited

U.S. PATENT DOCUMENTS

2016/0367492 A1 12/2016 Yoo

FOREIGN PATENT DOCUMENTS

| CN | 106456563 A | 2/2017 |
|---|---|---|
| FR | 2883170 A1 | 9/2006 |
| TW | I666214 B | 7/2019 |

OTHER PUBLICATIONS

Hong et al., 2022, abstract from ACS Applied Materials and Interfaces, 2022, 14(3), 3849-3863.*
Shekter et al., 2007, caplus an 2007:708954.*
Yu-Jen Chen et al., "Activation of Angiogenesis and Wound Healing in Diabetic Mice Using NO-Delivery Dinitrosyl Iron Complexes," Mol. Pharmaceutics, vol. 16(10), published on Aug. 22, 2019.pp. 4241-4251.
Yi-Po Chen, et al. "Application of Dinitrosyl Iron Complex (DNIC) in Angiogenesis, Wound Healing and Anticancer Activity," Chemistry, Dec. 1, 2019; 16 pages., vol. 77.4.

* cited by examiner

*Primary Examiner* — Sun Jae Yoo
(74) *Attorney, Agent, or Firm* — MUNCY GEISSLER OLDS & LOWE P.C.

(57) ABSTRACT

An external dermal composition and a method for beautifying skin are provided. The external dermal composition mainly includes a double nitrosyl-iron complex and a pharmaceutically acceptable additive. The external dermal composition delivers nitric oxide to a user's skin to beautify the skin when applied to the user's skin.

13 Claims, 17 Drawing Sheets
(4 of 17 Drawing Sheet(s) Filed in Color)

EXTERNAL DERMAL COMPOSITION AND METHOD FOR BEAUTIFYING SKIN

CROSS-REFERENCE TO RELATED APPLICATION

This application claims the benefit of Taiwan Patent Application Serial No. 110133933 filed on Sep. 12, 2021, the subject matter of which is incorporated herein by reference.

BACKGROUND OF THE INVENTION

1. Field of the Invention

The present invention relates to an external dermal composition and a method for beautifying skin; particularly, to an external dermal composition for delivering a double nitrosyl-iron complex to a user's skin and a method for beautifying the user's skin using the external dermal composition the double comprising the double nitrosyl-iron complex.

2. Description of Related Art

Nitric oxide (NO) is a biologically active gas molecule that has been proved to have many physiological functions, such as anti-inflammatory and anti-apoptosis. At present, the FDA-approved nitric oxide reagents can be administered via sublingual administration, inhalation, intravenous injection, or intravenous infusion. Oral administration is relatively a convenient route for administration; however, reagent for dermal application directly to the skin has not been developed because nitric oxide is unstable.

For this reason, an external dermal composition containing double nitrosyl-iron complex, which has low toxicity and is not irritating to the skin. The external dermal composition may release nitric oxide when applied to the user's skin to achieve the purpose of beautifying the skin by promoting skin collagen production, promoting skin wound healing, promoting skin regeneration, and inhibiting skin melanin production.

SUMMARY OF THE INVENTION

The present invention provides an external dermal composition, comprising a double nitrosyl-iron complex, and a pharmaceutically acceptable additive:

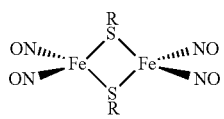

(I)

wherein R represents a $C_1$-$C_5$ carboxyl group.

In one embodiment, the pharmaceutically acceptable additive is at least one selected from a group consisting of water, glycerin, wax, alcohol, vegetable oil, mineral oil, silicone, fatty ester, fatty alcohol, ethylene glycol, polyethylene glycol, propylene glycol, and mixture thereof.

In one embodiment, the external dermal composition is in a form selected from a group consisting of an ointment, a lotion, a cream, a gel, a suspension, a spray, a powder, and a foaming agent.

In one embodiment, the weight percentage of the double nitrosyl-iron complex is 0.1-20% based on the total weight of the external dermal composition.

In one embodiment, when the external dermal composition is applied to the skin of a user, the double nitrosyl-iron complex in the external dermal composition delivers nitric oxide to the skin.

In one embodiment, R is a $C_3$ carboxyl group.

The present invention further provides a method for beautifying skin, comprising: applying a double nitrosyl-iron complex of formula (I) to a user's skin:

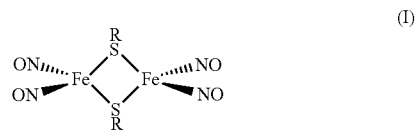

(I)

wherein R represents a $C_1$-$C_5$ carboxyl group.

In one embodiment, the double nitrosyl-iron complex of formula (I) in the external dermal composition delivers nitric oxide to the skin when the external dermal composition is applied to the user's skin.

In one embodiment, beautifying the skin refers to promoting skin collagen production, promoting skin wound healing, promoting skin regeneration, and inhibiting melanin production.

In one embodiment, the external dermal composition further comprises a pharmaceutically acceptable additive, wherein the pharmaceutically acceptable additive is at least one selected from a group consisting of water, glycerin, wax, alcohol, vegetable oil, mineral oil, silicone, fatty ester, fatty alcohol, ethylene glycol, polyethylene glycol, propylene glycol, and mixture thereof.

In one embodiment, the external dermal composition is in a form selected from a group consisting of an ointment, a lotion, a cream, a gel, a suspension, a spray, a powder, and a foaming agent.

In one embodiment, the weight percentage of the double nitrosyl-iron complex is 0.1-20% based on the total weight of the external dermal composition.

In one embodiment, R is a $C_3$ carboxyl group.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Hereafter, examples will be provided to illustrate the embodiments of the present invention. The advantages and effects of the invention will become more apparent from the disclosure of the present invention. Other various aspects also may be practiced or applied in the invention, and various modifications and variations can be made without departing from the spirit of the invention based on various concepts and applications.

[Evaluation of Nitric Oxide Release Activity]

Figure 1:
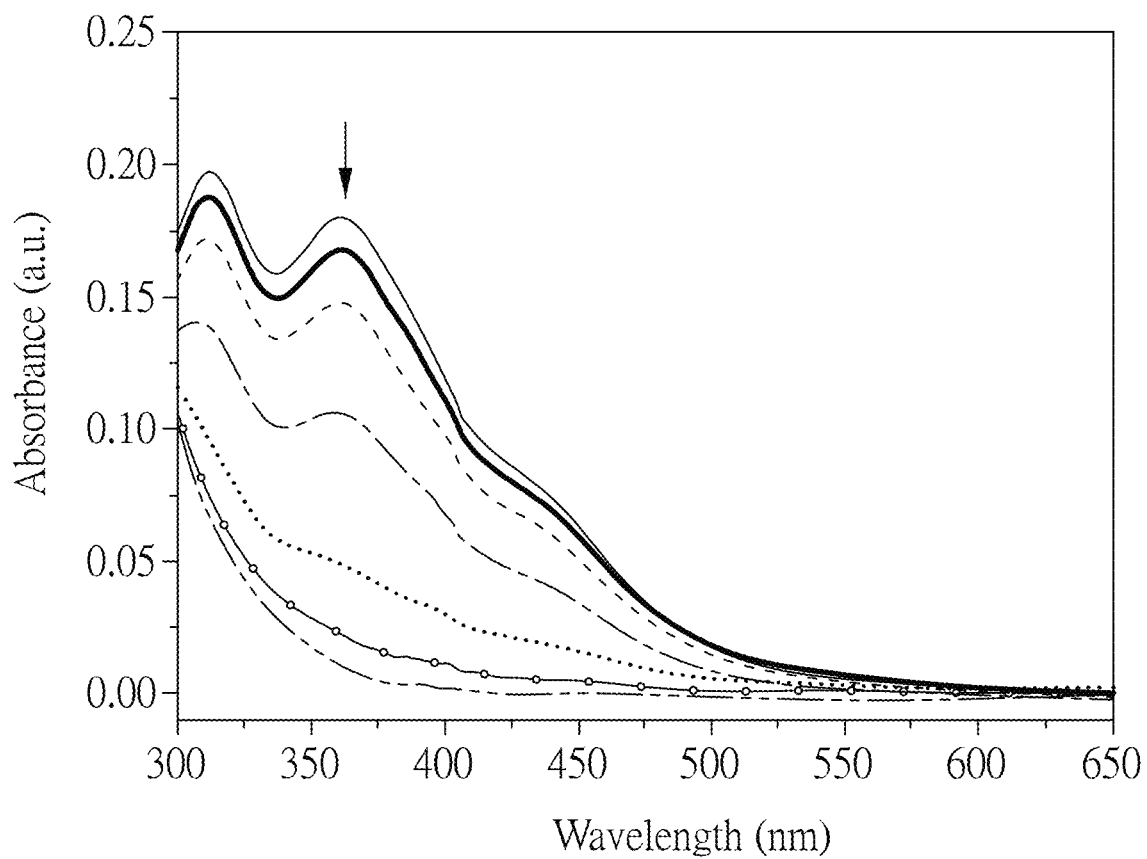
FIG. 1 is a UV-vis spectrum of the double nitrosyl-iron complex of different times of one embodiment of the present invention.
Figure 2:
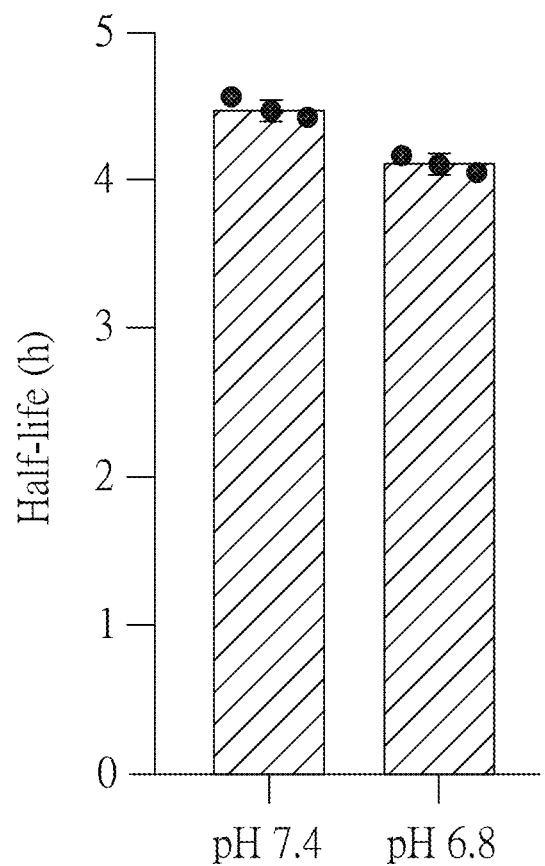
FIG. 2 is a schematic diagram of the half-life of the double nitrosyl-iron complex at different pH values of one embodiment of the present invention.
Figure 3:
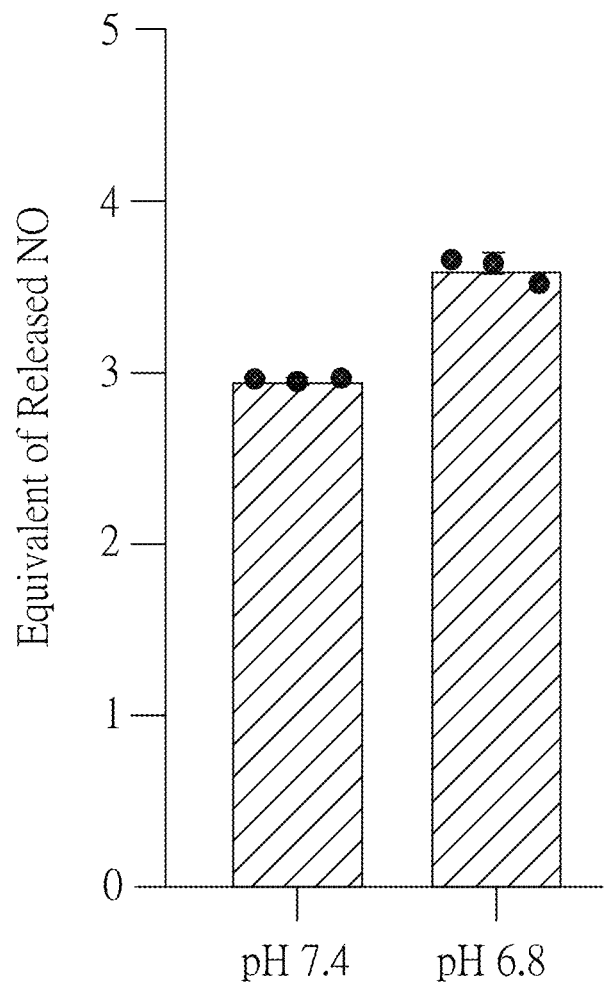
FIG. 3 is a schematic diagram of equivalents of nitric oxide released by the double nitrosyl-iron complex at different pH values of one embodiment of the present invention.

At a 37° C. aerobic environment, the absorbance at a wavelength of 362 nm of double nitrosyl-iron complexes (formula (I), wherein R is a $C_3$ carboxyl group) was measured at different time points and different pH values for evaluating its half-life. The results were shown in FIG. 1 to FIG. 3. From the evaluation results, it can be known that the half-life of the double nitrosyl-iron complex in an environment with a pH of 7.4 is 4.5±0.1 hours. The half-life in an environment with a pH of 6.8 is 4.1±0.1. In addition, the double nitrosyl-iron complexes can decompose 3-3.6 equivalents of nitric oxide on average at 37° C. in an aerobic environment.

[Cytotoxicity Test]

Human skin keratinocytes (HaCaT), human fibroblasts (CCD-966SK), and mouse melanoma cells (B16F10) were separately seeded into 96-well plates with $2\times10^5$ cells per well. After 24 hours of culture, each well was added with different concentrations of double nitrosyl-iron complexes (formula (I), wherein R is a $C_3$ carboxyl group), and after one day of culture, 10 μL of MTT (5 mg/mL dissolved in PBS) was added to each well. After 2 hours, a full-wavelength microdisk spectrophotometer was used to detect the absorbance of the purple triphenylmethyl ester (formazan) crystal at a wavelength of 570 nm.

Figure 4:
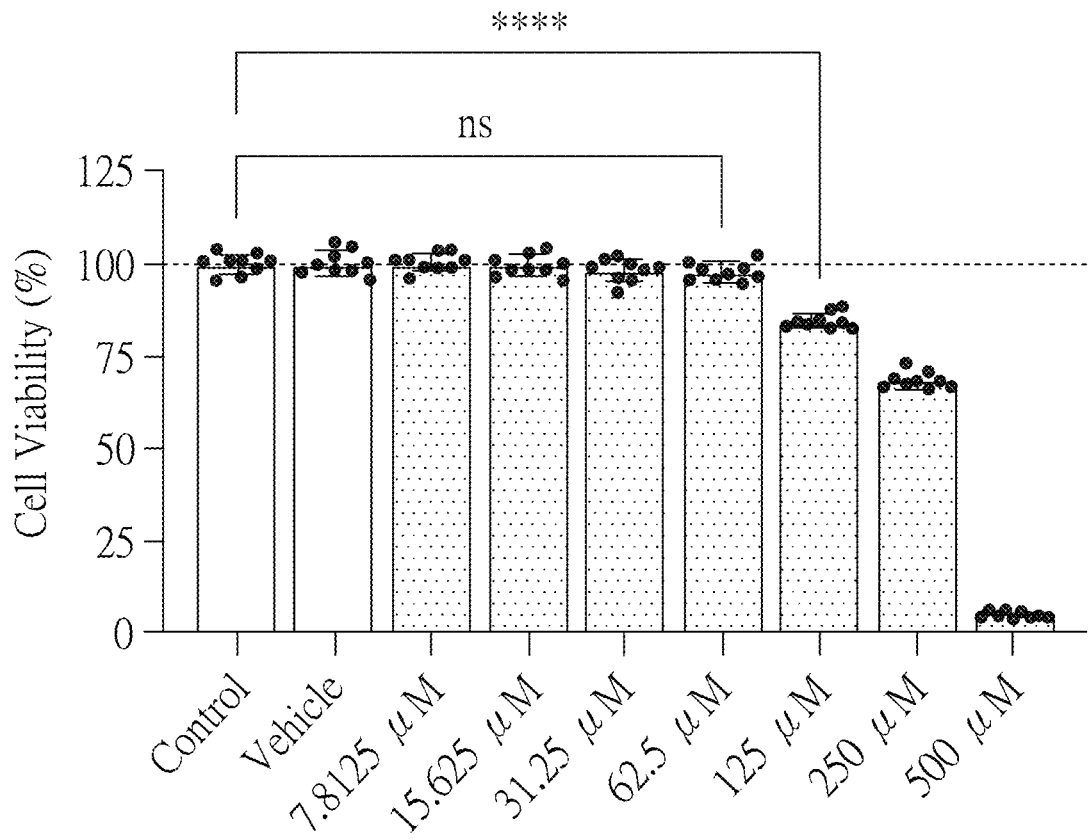
FIG. 4 shows the result of the cytotoxicity test of the double nitrosyl-iron complex on human skin keratinocytes of one embodiment of the present invention.
Figure 5:
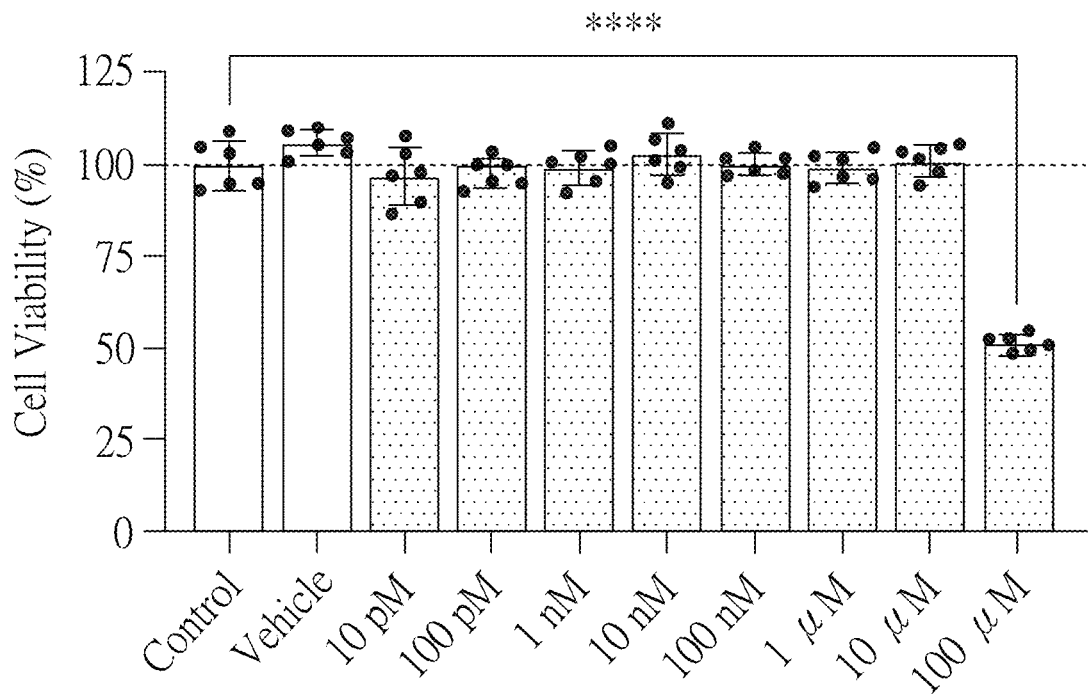
FIG. 5 shows the result of the cytotoxicity test of the double nitrosyl-iron complex on human fibroblast of one embodiment of the present invention.
Figure 6:
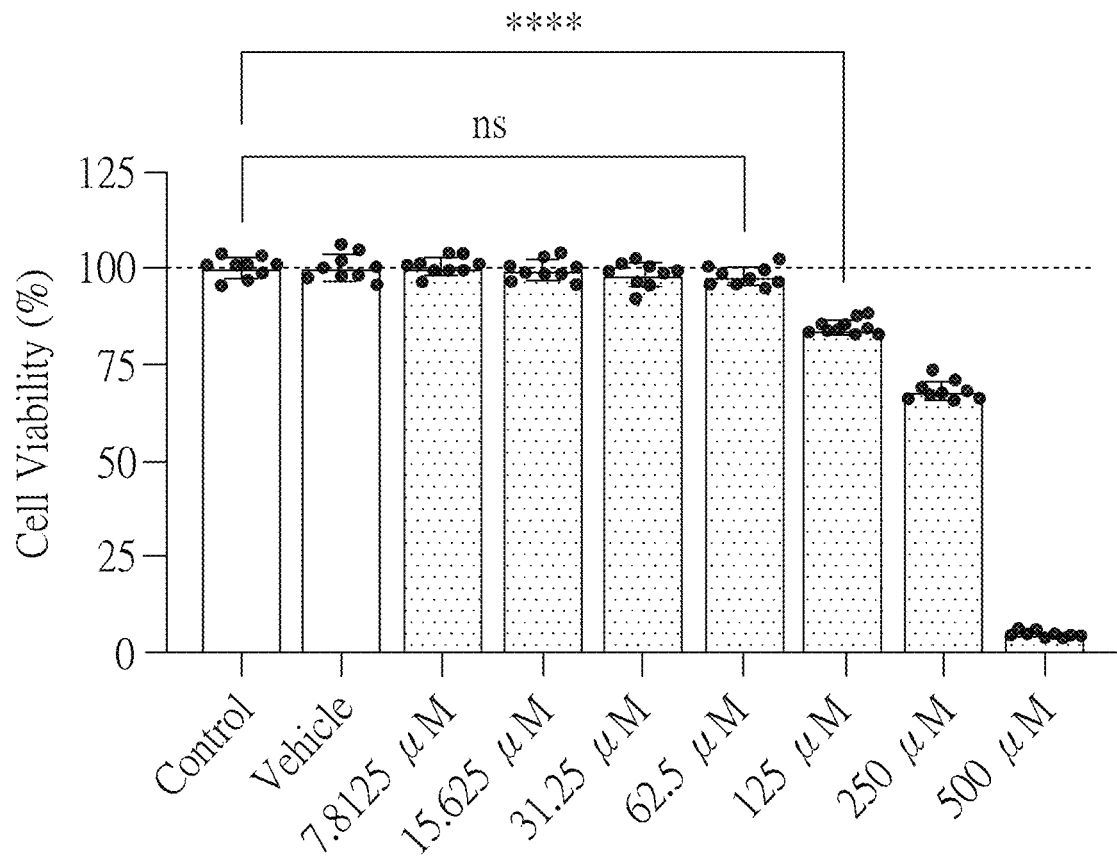
FIG. 6 shows the result of the cytotoxicity test of the double nitrosyl-iron complex on mouse melanoma cells of one embodiment of the present invention.

The cytotoxicity test results of human skin keratinocytes (HaCaT), human skin fibroblasts (CCD-966SK), and mouse skin melanoma cells (B16F10) treated with double nitrosyl-iron complex are shown in FIG. 4 to FIG. 6. the experimental results showed that the half-maximal inhibitory concentration (IC50) for HaCaT cells was 350.2 μM; the IC50 value for CCD-966SK cells was 92.3 μM, and the IC50 value for B16F10 cells was 222.5 μM. According to the results, it is proved that the double nitrosyl-iron complex of the present invention has low cytotoxicity and does no harm to cells.

[Evaluation of Skin Irritation]

In the present evaluation, the EpiDerm™ SIT (EPI-200) was used for skin irritation tests following the OECD 439 test guidelines.

Figure 7:
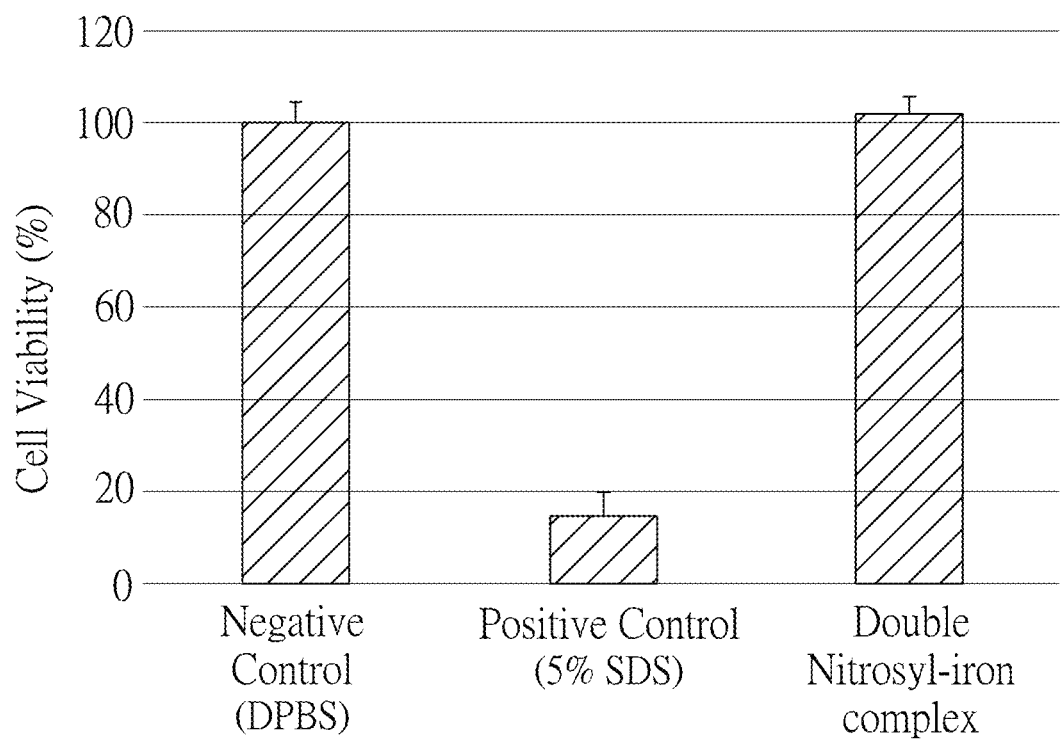
FIG. 7 shows the result of the skin irritation test of one embodiment of the present invention.

In the skin irritation test, the double nitrosyl-iron complex at a concentration of 50 μM was used as the test group, Dulbecco's Phosphate-Buffered Saline (DPBS) was used as the negative control group, and 5% of sodium dodecyl sulfate (SDS) solution was used as a positive control group. The test was repeated 3 times, and the average value was used for evaluation. The evaluation results were shown in FIG. 7. The tissue survival rate of the negative control group was 100%; the tissue survival rate of the positive control group was 15.11%, and the tissue survival rate of the 50 μM double nitrosyl-iron complex test group was 102.19%. Accordingly, double nitrosyl-iron complex was considered as non-skin irritation based on the in vitro irritation test.

[Evaluation of Eye Irritation]

In the present evaluation, the EpiOcular™ (OCL-200-EIT) was used for eye irritation tests following the OECD 492 test guidelines.

Figure 8:
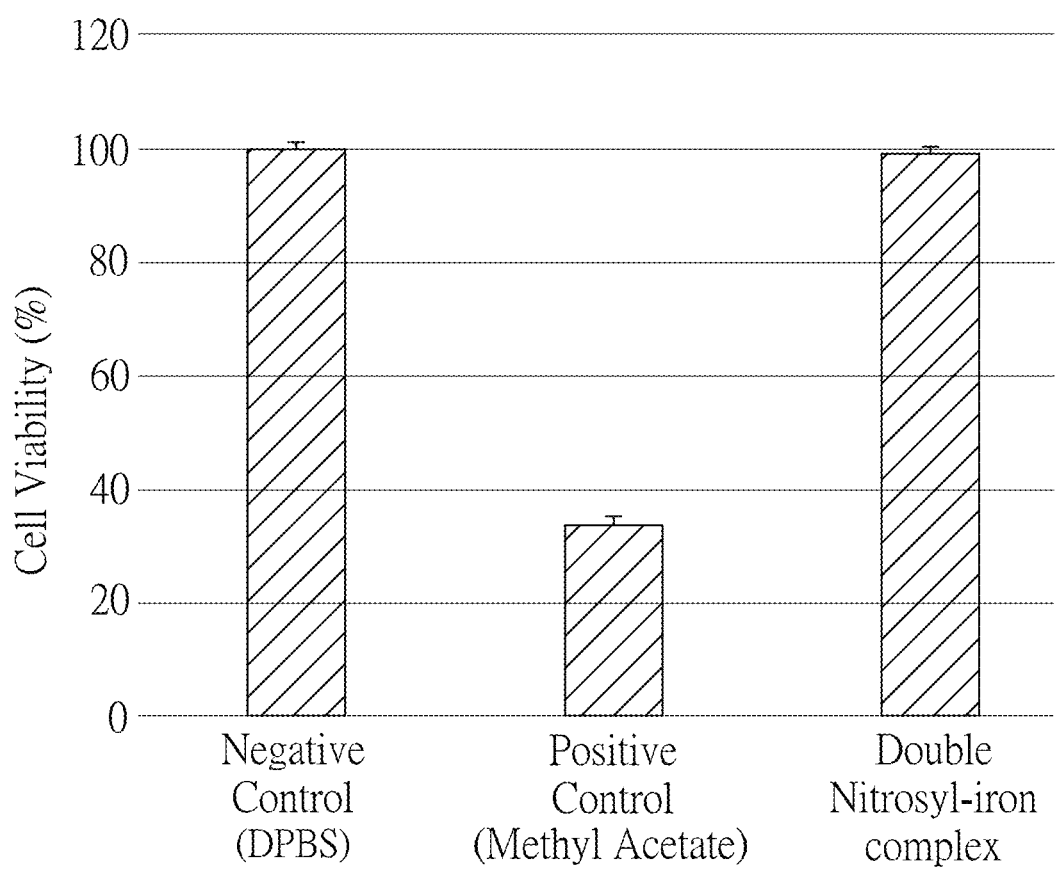
FIG. 8 shows the result of the eye irritation test of one embodiment of the present invention.

In the eye irritation test, the double nitrosyl-iron complex at a concentration of 50 μM was used as the test group, Dulbecco's Phosphate-Buffered Saline (DPBS) was used as the negative control group, and 100% of methyl acetate solution was used as a positive control group. The test was repeated 3 times, and the average value was used for evaluation. The evaluation results were shown in FIG. 8. The tissue survival rate of the negative control group was 100%, the tissue survival rate of the positive control group was 34.01%, and the tissue survival rate of the 50 μM double nitrosyl-iron complex test group was 99.37%. Accordingly, double nitrosyl-iron complex was considered as non-eye irritation based on the in vitro irritation test.

[Evaluation of Skin Cell Regeneration]

Figure 9:
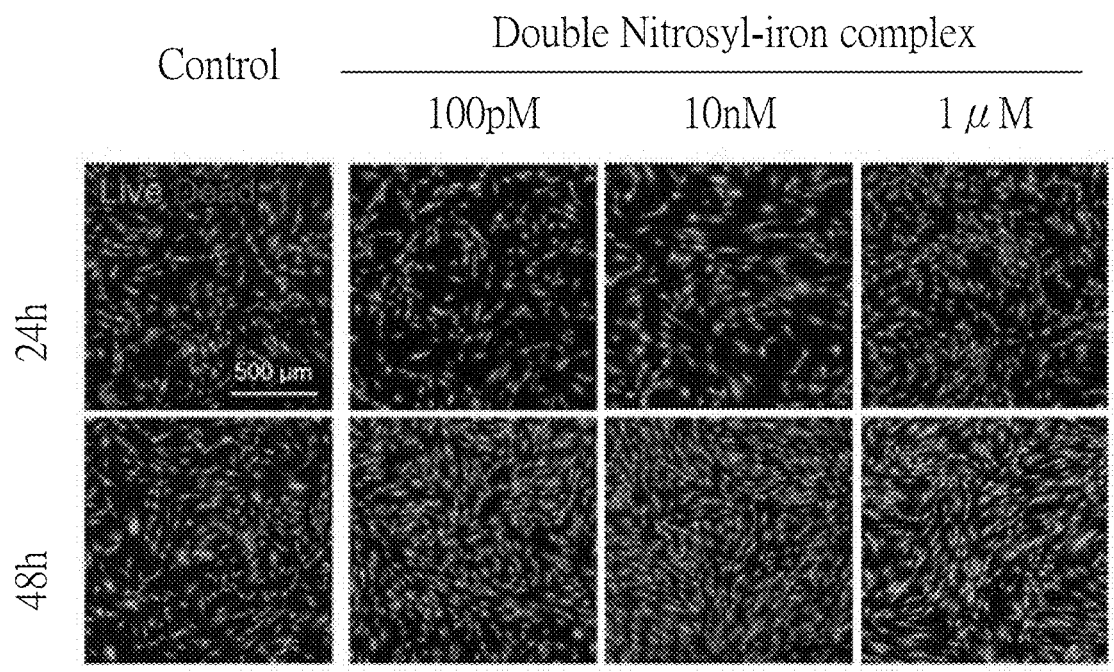
FIG. 9 shows the morphologies of the human fibroblasts of the cell proliferation experiment of one embodiment of the present invention.
Figure 10:
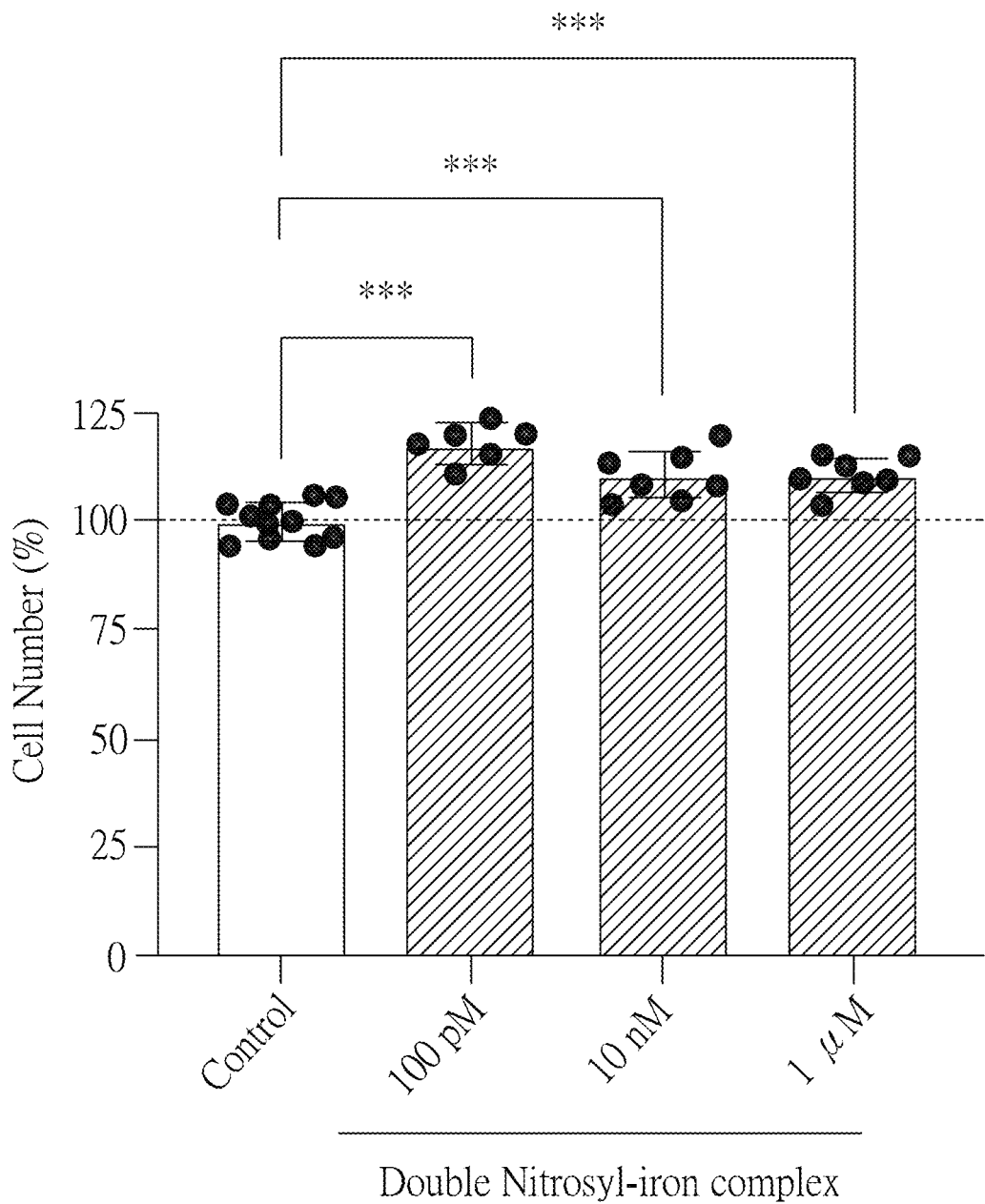
FIG. 10 shows the cell number of the human fibroblast of the cell proliferation experiment of one embodiment of the present invention.

Cell proliferation experiments were performed to evaluate the effect of the double nitrosyl-iron complex on skin cell regeneration. First, human fibroblasts (CCD-966SK) were cultured with the double nitrosyl-iron complex of different concentrations, and the cell number was counted after 24 hours and 48 hours of culture. FIG. 9 showed the morphologies of the cells after 24 hours and 48 hours of culture. The cell number after 48 hours of culture was shown in FIG. 10. According to the test results, it is proved that the double nitrosyl-iron complex has a significant effect on skin cell regeneration.

[Evaluation of Skin Wound Healing]

Human fibroblasts (CCD-966SK) were cultured in a 24-well plate, and $4\times10^5$ cells were added to each well. After culturing for 10 hours to completely cover the orifice plate, the tip of a P200 micro dispenser was used to scrape out a linear defect with a fixed width in the center of the orifice plate. After the damage is established, medium containing various concentrations of the double nitrosyl-iron complex was added to each well, then, observe the healing of the damaged area to understand whether the double nitrosyl-iron complex can promote fibroblasts cell migration.

Figure 11:
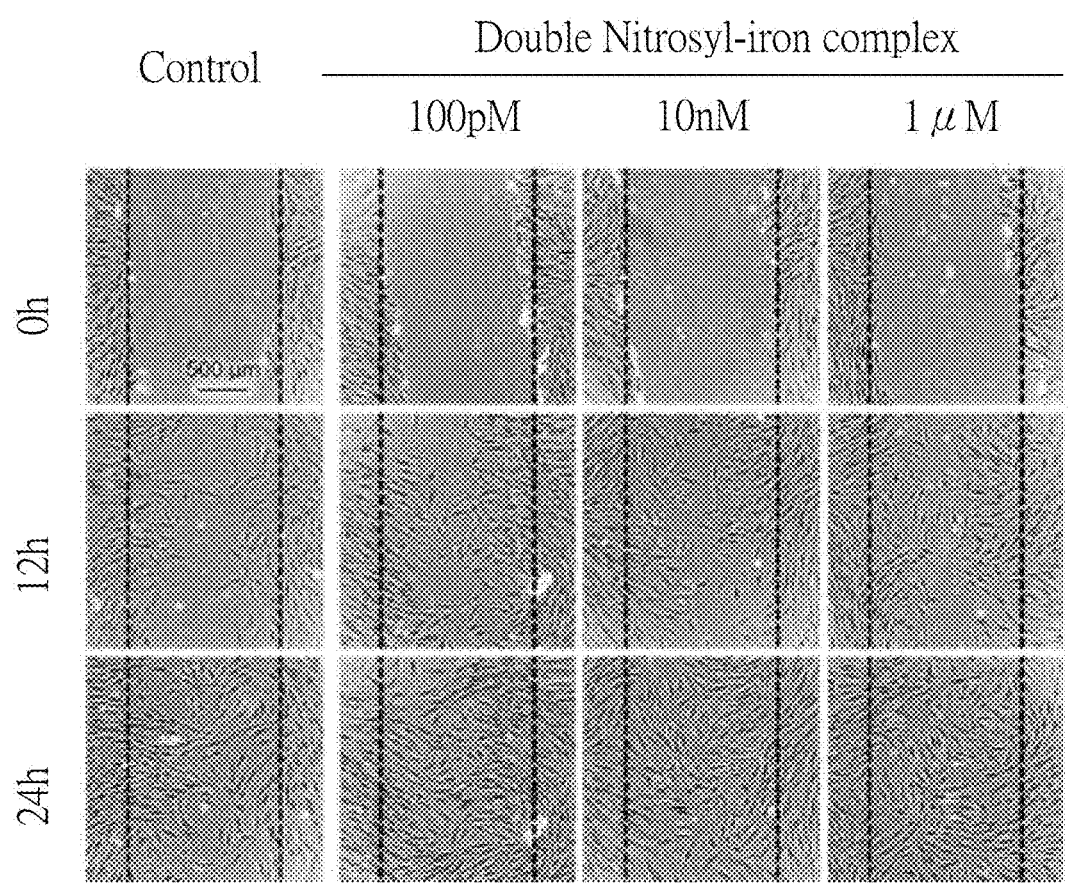
FIG. 11 shows the cell morphology of the human fibroblast of the wound healing test of one embodiment of the present invention.
Figure 12:
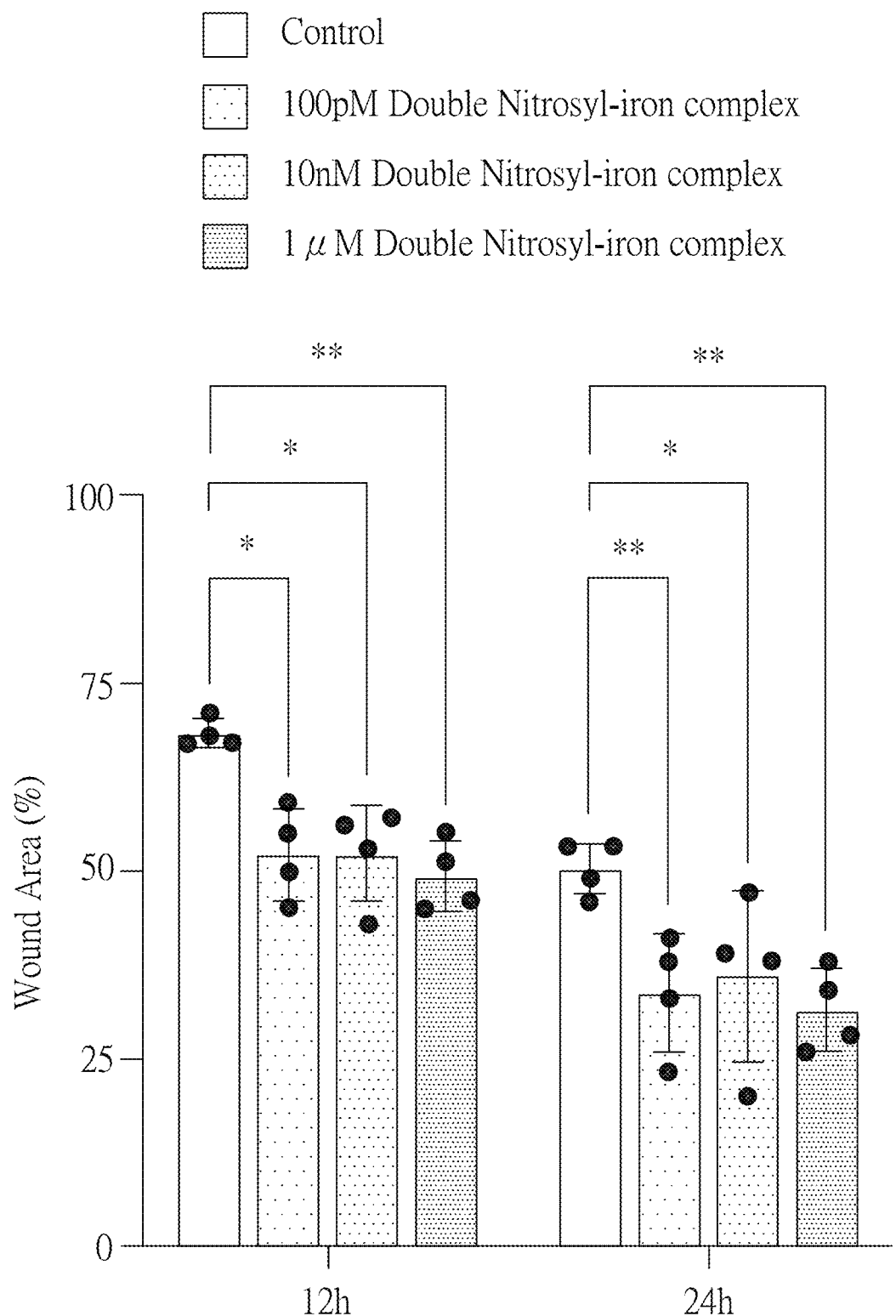
FIG. 12 shows the cell number of the human fibroblast of the wound healing test of one embodiment of the present invention.

The cell morphology of the skin wound repair test was shown in FIG. 11, and the statistical results were shown in FIG. 12. According to the test results, it is proved that the addition of 100 pM, 10 nM, and 1 µM double nitrosyl-iron complex to the human fibroblasts (CCD-966SK) all have the effect of promoting cell migration and have a significant effect on skin wound healing.

[Evaluation of Skin Collagen Production]

Human fibroblasts (CCD-966SK) were cultured in a 48-well plate, and 7500 cells were added to each well. Subsequently, medium containing various concentrations of the double nitrosyl-iron complex was added to each well every 24 hours, and Sirius red was used for staining on the $7^{th}$ day to observe and quantify the amount of collagen production.

Figure 13:
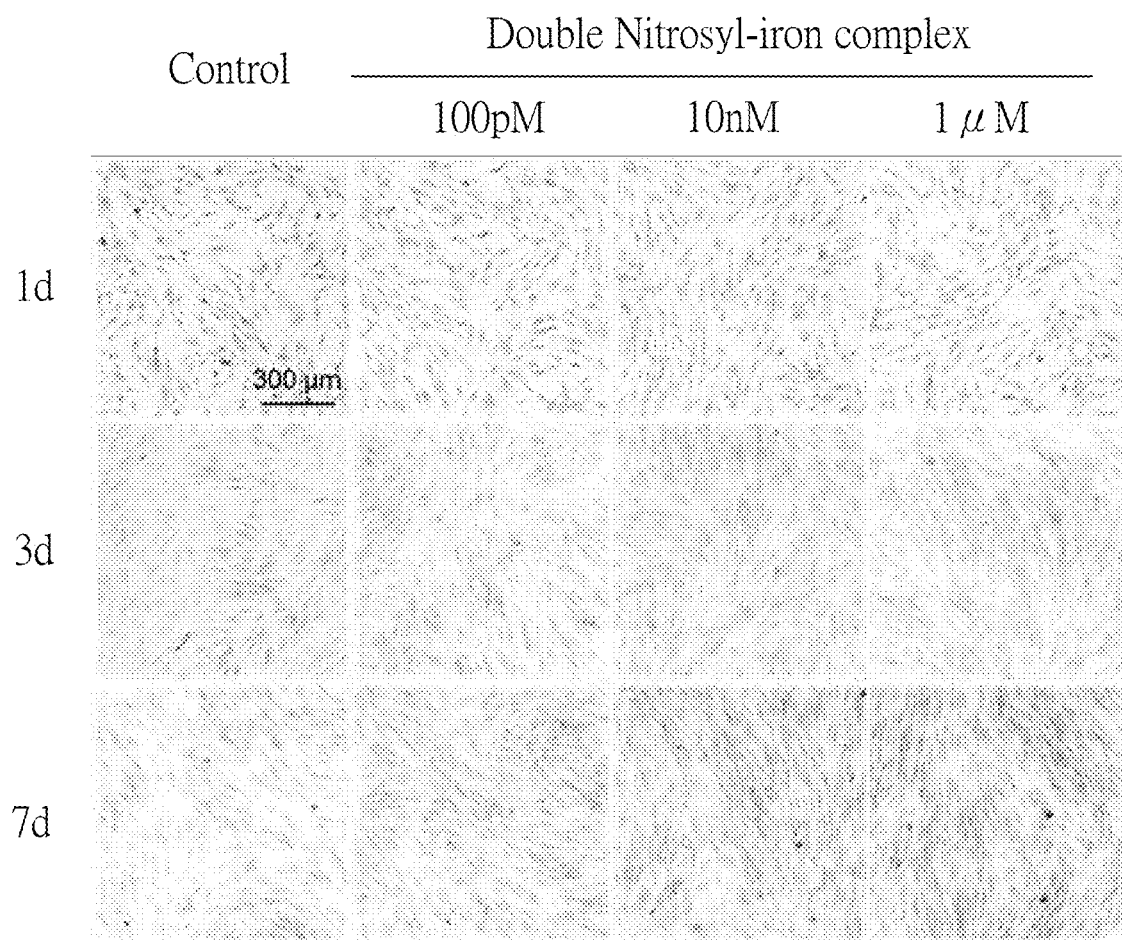
FIG. 13 shows the cell staining images of the human fibroblast of the collagen production test of one embodiment of the present invention.
Figure 14:
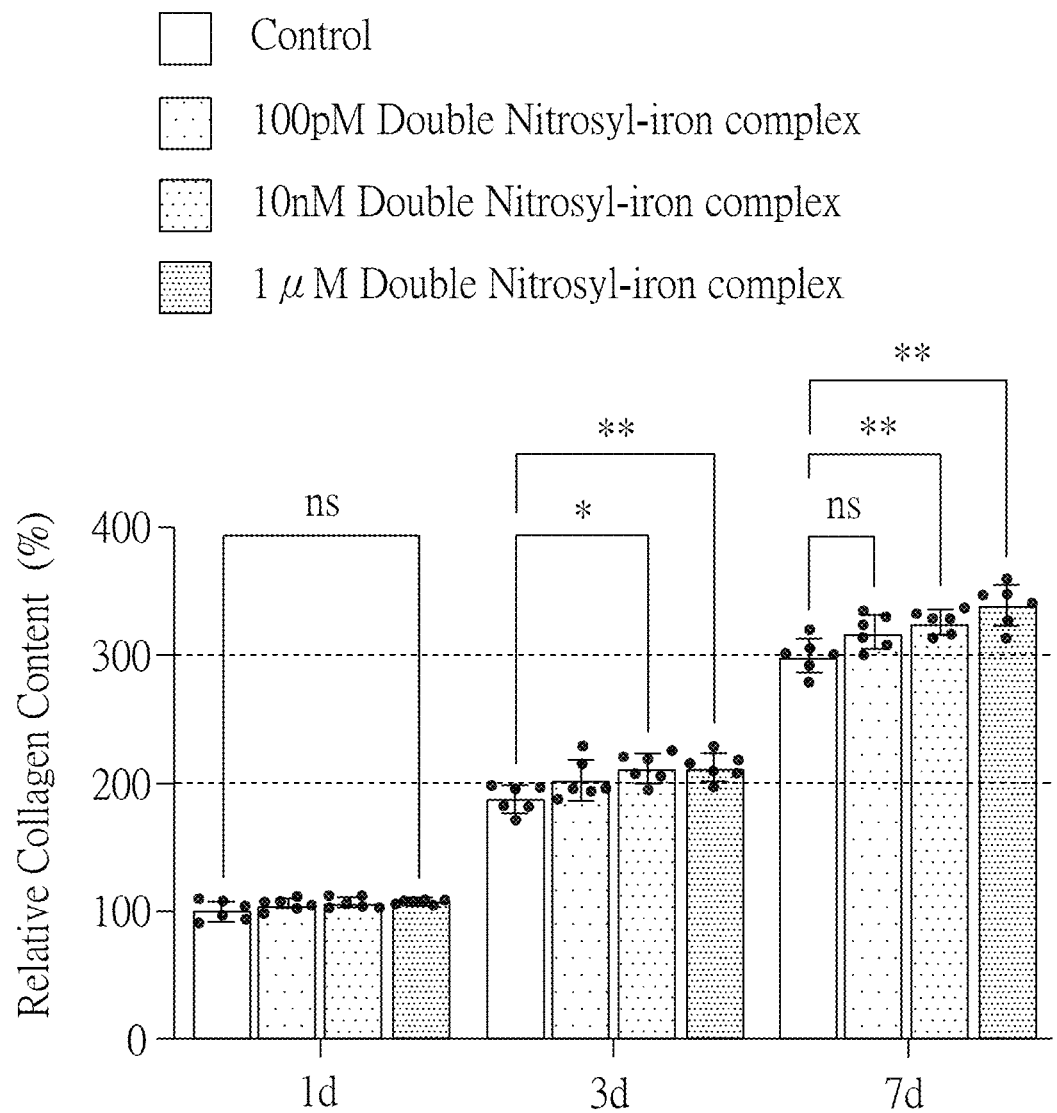
FIG. 14 shows the collagen content analysis result of the collagen production test of one embodiment of the present invention.

The cell staining images of the first type and third type collagen regeneration experiments were shown in FIG. 13, wherein the red color indicates collagen secretion. The statistical results are shown in FIG. 14. According to the results, it is proved that human fibroblasts (CCD-966SK) cultured with 100 pM, 10 nM, and 1 µM double nitrosyl-iron complex all have the effect of promoting collagen production.

[Evaluation of Skin Melanin Production]

Mouse melanoma cells (B16F10) were cultured in a 12-well plate, and $4\times10^4$ cells were added to each well. After 24 hours of incubation, α-melanocyte-stimulating hormone was added to each well, and medium containing arbutin or various concentrations of the double nitrosyl-iron complex was added. After culturing for 48 hours, the cells were freed by trypsin and collected by centrifugation. The cells were centrifuged again after adding sodium hydroxide and incubating at 70° C. for 1 hour, and a full-wavelength microdisk spectrophotometer was used to detect the absorbance of the supernatant at a wavelength of 405 nm.

Figure 15:
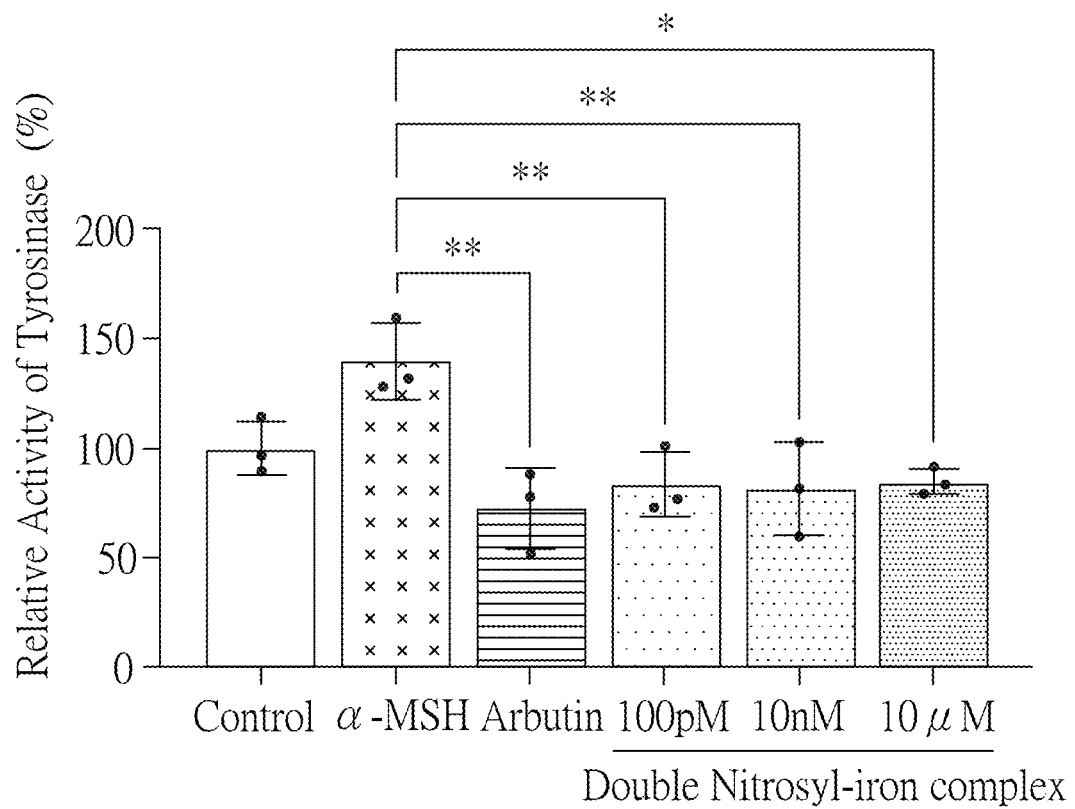
FIG. 15 shows the analysis result of the relative activity of tyrosinase in mouse melanoma cells of one embodiment of the present invention.
Figure 16:
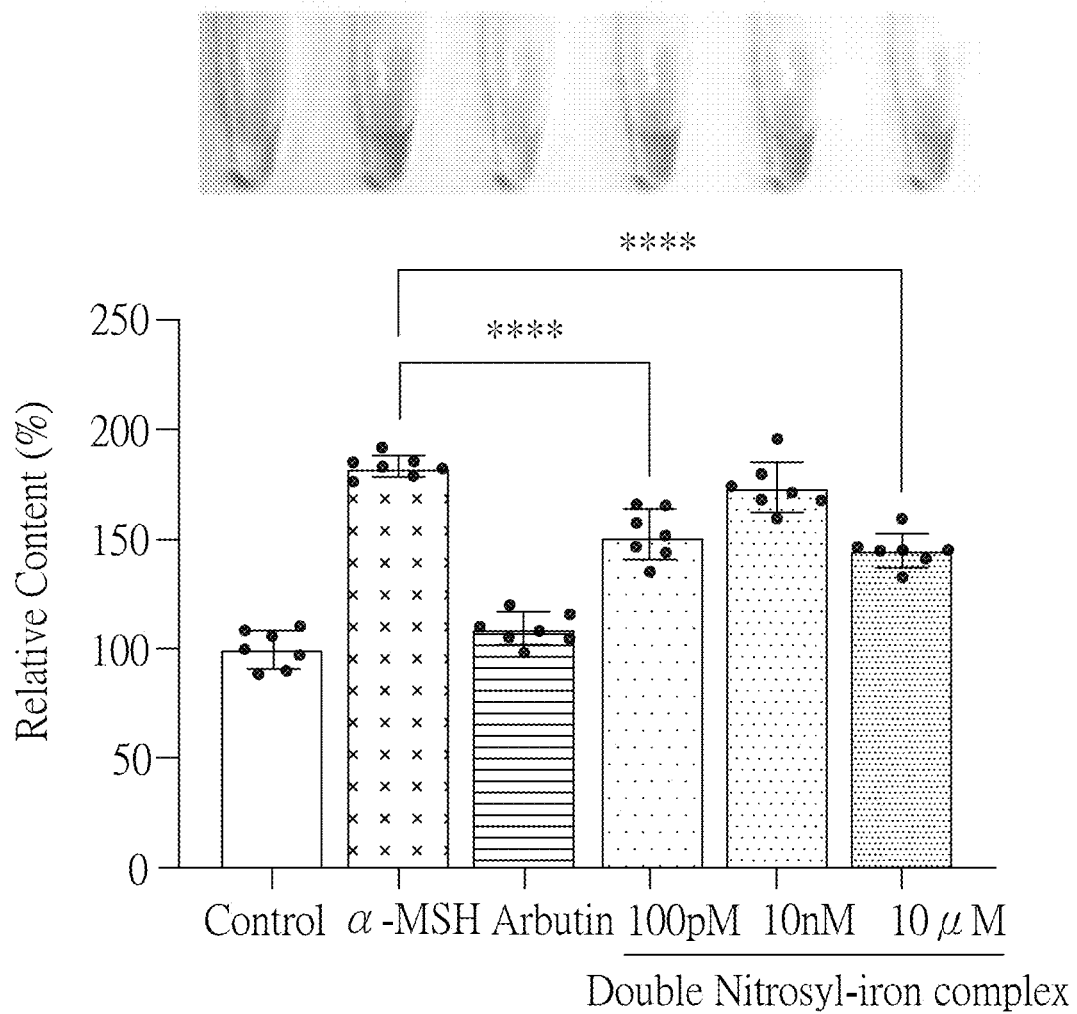
FIG. 16 shows the relative content of melanin in mouse melanoma cells of one embodiment of the present invention.
Figure 17:
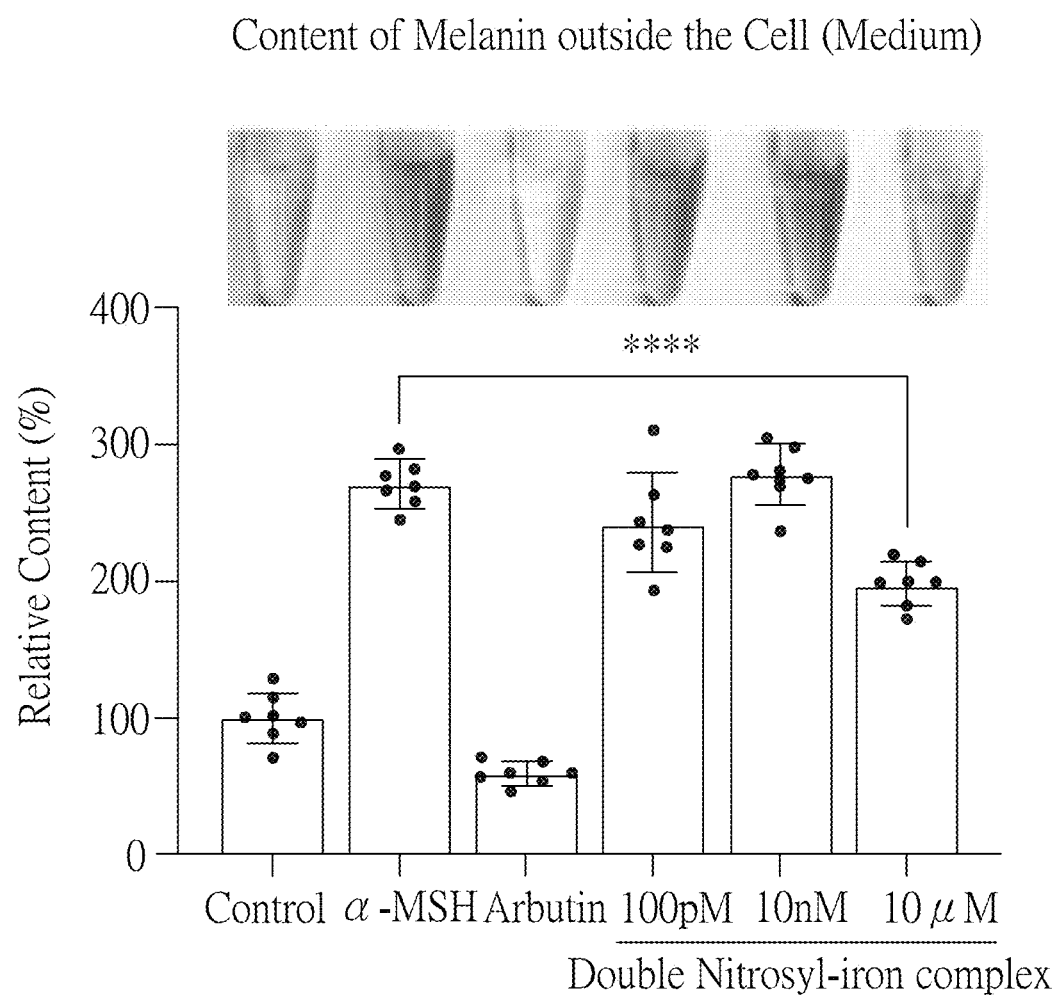
FIG. 17 shows the relative content of melanin outside mouse melanoma cells of one embodiment of the present invention.

According to the relative activity of tyrosinase shown in FIG. 15, and the relative content of melanin inside and outside the cell were shown in FIG. 16 and FIG. 17, respectively, it can be noted that the addition of different concentrations of the double nitrosyl-iron complex has the effect of inhibiting the production of tyrosinase and melanin in mole mouse melanoma cells (B16F10) supplemented with α-melanocyte-stimulating hormone.

Based on the above evaluation results, it can be inferred that the double nitrosyl-iron complex provided in the present invention can stably release nitric oxide after being applied to the skin, and has obvious effects on beautifying the skin, which refers to promoting skin regeneration, skin wound healing, skin collagen production, and inhibiting the production of melanin.

What is claimed is:

1. An external dermal composition, comprising a double nitrosyl-iron complex, and a pharmaceutically acceptable additive:

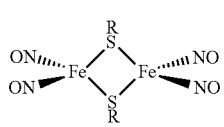

(I)

wherein R represents a $C_1$-$C_5$ carboxyl group.

2. The external dermal composition of claim 1, wherein the pharmaceutically acceptable additive is at least one selected from a group consisting of water, glycerin, wax, alcohol, vegetable oil, mineral oil, silicone, fatty ester, fatty alcohol, ethylene glycol, polyethylene glycol, propylene glycol, and mixture thereof.

3. The external dermal composition of claim 1, wherein the external dermal composition is in a form selected from a group consisting of an ointment, a lotion, a cream, a gel, a suspension, a spray, a powder, and a foaming agent.

4. The external dermal composition of claim 1, wherein the weight percentage of the double nitrosyl-iron complex is 0.1-20% based on the total weight of the external dermal composition.

5. The external dermal composition of claim 1, wherein when the external dermal composition is applied to skin of a user, the double nitrosyl-iron complex in the external dermal composition delivers nitric oxide to the skin.

6. The external dermal composition of claim 1, wherein R is a $C_3$ carboxyl group.

7. A method for beautifying skin, comprising: applying an external dermal composition comprising a double nitrosyl-iron complex of formula (I) to a user's skin:

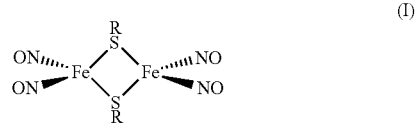

(I)

wherein R represents a $C_1$-$C_5$ carboxyl group.

8. The method of claim 7, wherein the double nitrosyl-iron complex of formula (I) in the external dermal composition delivers nitric oxide to the skin when the external dermal composition is applied to the user's skin.

9. The method of claim 8, wherein beautifying the skin refers to promoting skin collagen production, promoting skin wound healing, promoting skin regeneration, and inhibiting melanin production.

10. The method of claim 7, wherein the external dermal composition further comprises a pharmaceutically acceptable additive, wherein the pharmaceutically acceptable additive is at least one selected from a group consisting of water, glycerin, wax, alcohol, vegetable oil, mineral oil, silicone, fatty ester, fatty alcohol, ethylene glycol, polyethylene glycol, propylene glycol, and mixture thereof.

11. The method of claim 7, wherein the external dermal composition is in a form selected from a group consisting of an ointment, a lotion, a cream, a gel, a suspension, a spray, a powder, and a foaming agent.

12. The method of claim 7, wherein the weight percentage of the double nitrosyl-iron complex is 0.1-20% based on the total weight of the external dermal composition.

13. The method of claim 7, wherein R is a $C_3$ carboxyl group.

* * * * *